US006793639B2

(12) United States Patent
Gibbs et al.

(10) Patent No.: US 6,793,639 B2
(45) Date of Patent: Sep. 21, 2004

(54) PELVIC SPLINT AND ASSOCIATED METHOD

(75) Inventors: Michael A. Gibbs, Charlotte, NC (US); Michael Bosse, Charlotte, NC (US); John Marx, Charlotte, NC (US); Steven Colucciello, Charlotte, NC (US); David Jacobs, Matthews, NC (US); Barbara Ozmar, Charlotte, NC (US)

(73) Assignee: Charlotte-Mecklenburg Hospital Authority, Charlotte, NC (US)

( * ) Notice: Subject to any disclaimer, the term of this patent is extended or adjusted under 35 U.S.C. 154(b) by 0 days.

(21) Appl. No.: 10/300,976

(22) Filed: Nov. 21, 2002

(65) Prior Publication Data

US 2003/0073942 A1 Apr. 17, 2003

Related U.S. Application Data

(63) Continuation of application No. 09/447,165, filed on Nov. 22, 1999, now Pat. No. 6,503,217, which is a continuation-in-part of application No. 09/243,181, filed on Feb. 2, 1999, now abandoned.

(51) Int. Cl.[7] .................................................. A61F 5/00
(52) U.S. Cl. ........................................ 602/23; 128/869
(58) Field of Search ................................ 602/5, 23–25, 602/60–61, 75; 128/846, 311–312, 465, 467, 96.1, 99.1, 100.1, 869, 875; 2/311–312, 465, 467

(56) References Cited

U.S. PATENT DOCUMENTS

| 1,719,068 A | * | 7/1929 | McCormick et al. |
| 1,916,789 A | | 7/1933 | Fordham |
| 2,062,131 A | * | 11/1936 | Hirsch |
| 2,501,900 A | * | 3/1950 | Herbener |
| 2,596,275 A | * | 5/1952 | Muller ......................... 602/61 |
| 3,186,405 A | | 6/1965 | Bailey et al. |
| 3,351,055 A | | 11/1967 | Gottfried |
| 3,362,402 A | * | 1/1968 | Loeffel et al. ................ 602/19 |
| 3,460,531 A | | 8/1969 | Gardner |
| 3,717,143 A | * | 2/1973 | Johnson ....................... 602/19 |
| 3,745,998 A | | 7/1973 | Rose |
| 3,783,879 A | * | 1/1974 | Stalder ....................... 128/570 |
| 3,920,008 A | * | 11/1975 | Lehman ....................... 128/96 |
| 4,576,154 A | | 3/1986 | Hyman et al. |
| 4,580,555 A | * | 4/1986 | Coppess .................... 128/89 R |
| 4,624,248 A | | 11/1986 | Poole et al. |
| 4,657,003 A | | 4/1987 | Wirtz |
| 4,768,501 A | | 9/1988 | George |

(List continued on next page.)

FOREIGN PATENT DOCUMENTS

GB          765 416 A          1/1957

*Primary Examiner*—Nicholas D. Lucchesi
*Assistant Examiner*—Huong Q. Pham
(74) *Attorney, Agent, or Firm*—Alston & Bird LLP

(57) ABSTRACT

A pelvic splint for immobilizing and maintaining the annular integrity of the pelvis in the event of a pelvic ring fracture. The pelvic splint extends from about 5–10 cm above the iliac crest down to about the middle third of the thighs and substantially encircles the pelvis of the victim. The splint is then secured about the pelvis of the victim with two or more adjustable straps. The splint comprises a flexible casing having at least one pliable padding layer disposed therein and a plurality of flexible members individually disposed in pockets spaced apart about the casing. Once tightly secured around the pelvis by the adjustable straps, the splint conforms to the contours of the victim's pelvic area and stabilizes the pelvis by preventing lateral movement and constraining the pelvis in such a manner to preserve the annular integrity thereof. An associated method of stabilizing a pelvis is also disclosed.

5 Claims, 3 Drawing Sheets

U.S. PATENT DOCUMENTS

| | | | | |
|---|---|---|---|---|
| 4,884,562 A | * | 12/1989 | Stone | 128/78 |
| 4,926,502 A | * | 5/1990 | Miyamura | 2/44 |
| 5,086,514 A | | 2/1992 | Ross | |
| 5,121,756 A | | 6/1992 | Koledin | |
| 5,188,585 A | * | 2/1993 | Peters | 602/19 |
| 5,274,846 A | | 1/1994 | Kolsky | |
| 5,407,421 A | | 4/1995 | Goldsmith | |
| 5,407,422 A | | 4/1995 | Matthijs et al. | |
| 5,410,755 A | | 5/1995 | Obujen | |
| 5,437,618 A | | 8/1995 | Sikes | |
| 5,500,952 A | * | 3/1996 | Keyes | 2/2 |
| 5,830,167 A | | 11/1998 | Jung | |
| 5,840,050 A | | 11/1998 | Lerman | |
| 5,928,175 A | * | 7/1999 | Tanaka | 602/75 |
| 5,950,628 A | | 9/1999 | Dunfee | |
| 6,503,217 B1 | * | 1/2003 | Gibbs et al. | 602/23 |

* cited by examiner

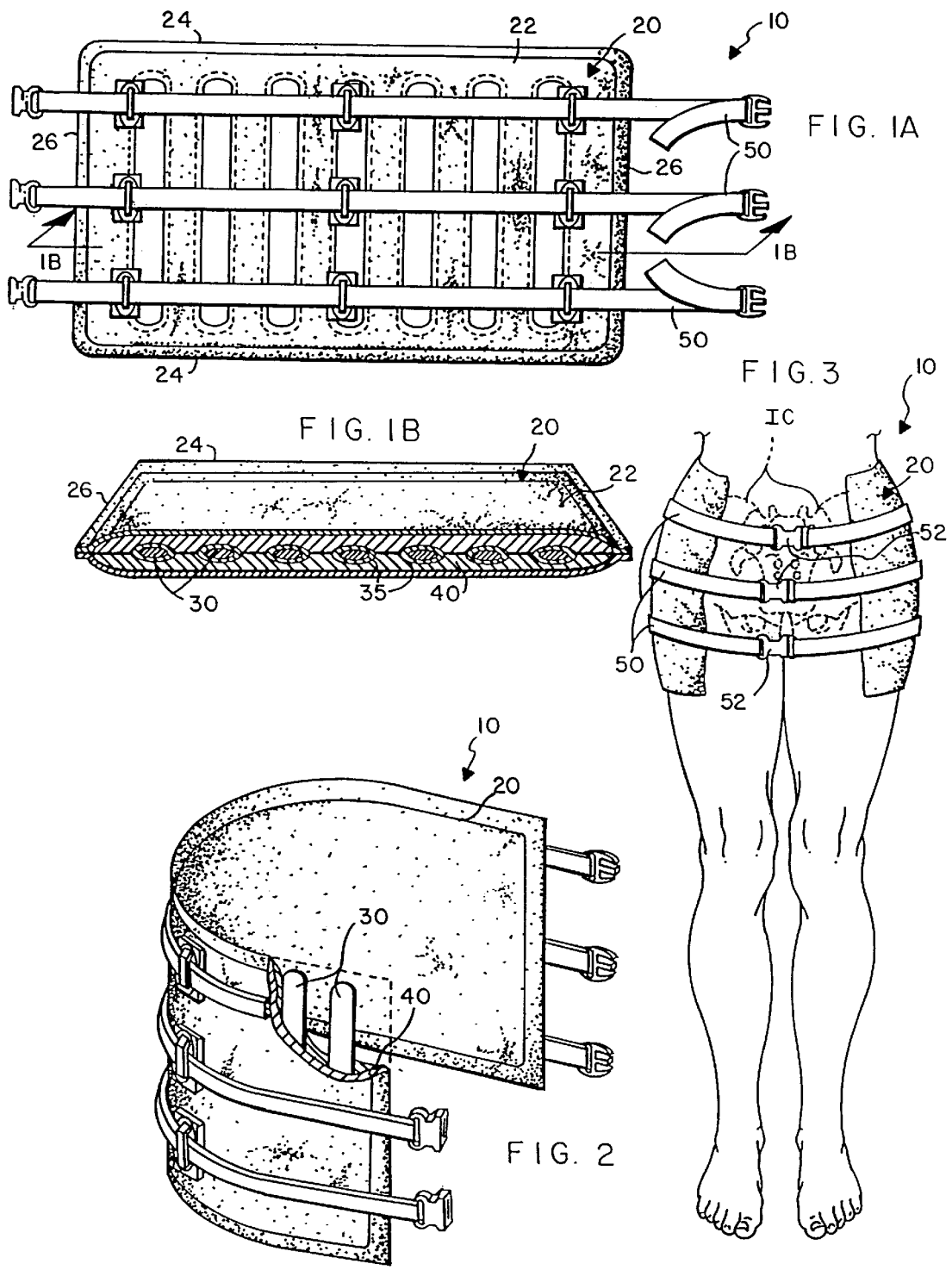

PELVIC SPLINT AND ASSOCIATED METHOD

CROSS-REFERENCES TO RELATED APPLICATIONS

This application is a continuation of U.S. patent application Ser. No. 09/447,165; filed Nov. 22, 1999, now U.S. Pat. No. 6,503,217 which is a continuation-in-part of U.S. patent application Ser. No. 09/243,181, filed on Feb. 2, 1999, now abandoned, both of which are hereby incorporated herein in their entirety by reference.

FIELD OF THE INVENTION

The present invention relates to splints for immobilizing the pelvic area of the body and, more particularly, to a pelvic splint used to stabilize the pelvis by immobilizing the same in order to maintain the annular integrity thereof in the event of a pelvic ring fracture injury and associated method.

BACKGROUND OF THE INVENTION

The human pelvis comprises three pelvic bones which combine to form a strong anatomic ring. When a victim experiences a major trauma, the injuries may include pelvic fractures which will disrupt the integrity and stability of the pelvic ring. Pelvic fractures which disrupt the integrity of the pelvic ring generally lead to significant pelvic bleeding in the victim since the arteries and major veins passing through the pelvic area may easily be pinched, torn, or lacerated by the fractured bones. Pelvic bleeding is the major cause of death in victims with this injury. Thus, an immediate and important concern in early treatment of the victim is stabilization of the pelvis, which reduces bleeding, improves the comfort of the victim, and increases the victim's chances of survival. Most often, this early treatment comprises temporary measures which must be undertaken in the pre-hospital setting or in the emergency department before definitive surgical fixation of the pelvic fracture in the hospital setting. The temporary measure most often undertaken to stabilize the pelvis involves the use of a splint.

Splints come in a variety of sizes, shapes, and structures. These many devices generally share the same purpose of immobilizing the body in the event of an injury in order to prevent further damage, secondary injury, or undue agony to the person caused by unrestrained movement thereof. Most commonly, these splints are used to immobilize and prevent lateral displacement of the injured body part.

A backboard is a splint commonly used by emergency personnel for the purpose of immobilizing an injured victim, usually where the injury involves trauma to the neck, spine, and/or pelvis. The backboard is constructed of a rigid planar single-piece of material, wherein the victim is placed onto the backboard and secured thereto by a multitude of straps. Once secured to the backboard, the victim can be carried and loaded onto a stretcher for further transportation to a medical facility. However, as the victim is being transported on the backboard, the victim's body may often be subject to lateral forces due to flexing of the backboard, shifting of the body on the backboard between the straps, and the like. Thus, the victim may be subject to further injury or secondary trauma from lateral movement of the injured body part due to the shortcomings of the backboard in effectively immobilizing the victim. Thus, a common backboard is not particularly effective in addressing injuries to the pelvis.

Rigid splints may also come in pre-formed shapes to address an injury to a particular part of the body. For example, a neck brace may be constructed of rigid pre-formed materials and shaped into a form to encircle the neck area. The neck brace often extends from the head to the shoulders to prevent torsional as well as lateral movement therebetween. Such a concept could possibly be applied to a rigid pre-formed splint for stabilizing the pelvis. However, rigid splints are disadvantaged by limited adjustability and inability to adapt to various configurations of persons. Thus, multiple sizes must often be carried by emergency personnel and optimal fit of one of these sizes of splints on the victim is still not guaranteed. In addition, rigid pre-formed splints may cause storage problems on an emergency response vehicle where space is at a premium.

Generally, rigid splints are designed for a representative population and are not adaptable to conform to features of individual victims. Since these devices include rigid elements, they are often difficult to store and cumbersome to use. Ease of storage and/or use are often crucial considerations when these devices are provided for use by emergency response units. Further, these rigid splints may not completely and effectively immobilize the injured part of the victim's body due to poor fit or other reasons, leading to the possibility of exacerbation of the injury or secondary trauma. Thus, faced with the drawbacks of rigid splints, there exists a need for an alternative to a rigid splint having such features as complete immobilization of an injured body part, adjustability of fit, and ease of storage.

Another type of splint is an inflatable splint, which is typically used to immobilize injured extremities such as arms or legs. Generally, an inflatable splint comprises an air tight envelope assembly wrapped around the extremity and inflated to immobilize the same. The envelope assembly may comprise a single envelope or a plurality of connected envelope elements and is typically shaped to fit the body area for which it is intended. For example, an inflatable splint for a leg may be shaped as an inverted truncated cone, wherein the widest part of the cone is wrapped around the thigh, while the narrowest end is wrapped around the calf or ankle area. Once secured around the extremity, the envelope assembly is inflated and the expansion thereof immobilizes the injured extremity.

An example of an inflatable splint is disclosed by U.S. Pat. No. 3,186,405 to Bailey et al. and generally comprises multiple, generally tubular, parallel elements joined lengthwise to form a rectangular pad. The elements contain restrictors along their respective lengths in order to control the length of the element inflated. Adjacent elements are also manifolded together, enabling the splint to be inflated through a single valve. Once the pad has been applied to the afflicted area, a separate cover is placed over the pad to inwardly constrain the pad upon inflation. Both pad and cover wrap completely around the body part. Connectors spaced lengthwise along the longitudinal edges of both the pad and the cover secure the device around the afflicted body part and allow multiple devices to be joined together to expand the coverage of the splint. Further, connectors can be selectively unfastened to provide access to areas covered by the splint for examination thereof without having to remove the entire splint from the afflicted body part. In its uninflated state, this device is unobtrusive and easily stored.

However, inflatable splints typically impart pressure to the underlying injured extremity due to the nature of their operation. When inflated, the airtight envelope expands in the direction of least constraint. Since the surface of the inflatable splint in contact with the injured extremity should conform thereto, this surface is often the least constrained portion of the airtight envelope. Therefore, when inflated, the envelope will expand inward toward the injured extremity and impart pressure thereto. While pressure may be desirable in situations where the splint also acts as a compress for localized hemorrhaging or as a means for controlling blood pressure in the victim's body, it may also cause discomfort to the victim or disadvantageous restriction of blood circulation. The inflatable splint as disclosed in Bailey et al. is prone to these problems.

Further, even though applying pressure to the extremity may be desirable in some situations, the Bailey et al. splint is also cumbersome and difficult to use. First, the uninflated splint must be positioned and attached around the extremity, wherein both longitudinal ends are attached together by connectors. If the splint is not wide enough, a plurality of splints must be connected together to form a splint of the proper size to surround the extremity. Further, a cover must then be placed around the splint, wherein both longitudinal ends of the cover are attached together by connectors. After the splint and the cover have been applied, the splint is configured for the proper length by applying annular restrictive elements along the length thereof, typically at the location of adjacent restrictors. The restrictive elements constitute, for instance, strings which are tightly tied around the uninflated splint and cover. The restrictive elements control the length of the splint by closing the restrictors at a certain point along the tubular elements, wherein the remaining length of the tubular element is rendered uninflatable. Once the splint has been fitted on the extremity in this manner, it is then inflated to immobilize the extremity. Thus, this splint demonstrates that its use and adjustment on an individual may be difficult and cumbersome. As such, while the Bailey et al. splint may provide effective immobilization of the extremity and ease of storage in an emergency response vehicle, it also suffers from the drawbacks of lack of adjustability, both around the injured extremity and along the length thereof, and imparting sometimes unnecessary and unwanted pressure upon the injured extremity. Thus, in light of the Bailey et al. inflatable splint, there exists a need for an alternative type of splint which will effectively immobilize injured body parts without imparting pressure thereon when pressure is not necessary or comfortable for the victim, while being readily adjustable of fit various individuals and easily applied to the injured body part.

Still another type of splint is the vacuum immobilization splint. Vacuum immobilization splints generally consist of an airtight envelope having a port therein through which the envelope may be evacuated. Further, the envelope is at least partially filled with compressible discreet elements such as pliable expanded polymer beads. In practice, the envelope is wrapped about the afflicted body part and then evacuated via the port. Once evacuated, the envelope constricts around the beads and compresses the same. Friction between beads inside the envelope and between the beads and the inner surface of the envelope solidifies the shape of the evacuated envelope in the form in which it was wrapped about the injured extremity.

An example of a vacuum splint is shown in U.S. Pat. No. 5,121,756 to Koledin which discloses a vacuum immobilizer support for immobilizing and stabilizing the body of a victim. This splint comprises a flexible casing filled with compressible beads or other discrete elements, wherein the casing includes identifiable sections for the neck, thoracic, and pelvic regions. The flexible casing further includes a set parallel longitudinal stiffeners in the neck/thorax region and a separate set of parallel stiffeners in the pelvic region. An intermediate stiffener is provided between the two regions to prevent longitudinal shrinkage of the splint.

Koledin also discloses a vacuum immobilizer support wherein the victim is placed in the splint and the sides of the casing wrapped upward to contact the victim's sides. A continuous strap alternates between attachment points on the sides of the casing, wherein the strap is adjustable to hold the splint in place. The victim is placed in the desired position, from lying prone to sitting upright, and the casing then evacuated. Once evacuated, the casing becomes a rigid form, molded to the contours of and immobilizing the victim.

However, the splint disclosed in Koledin also displays some disadvantages. For instance, the pelvic section of this splint immobilizes and supports the lower body from the coccyx downward, while the neck/thorax section immobilizes and provides support for the spine or lumbar vertebrae in the thoracic region. A stiffener section is disposed between the neck/thorax section and the pelvic section of the splint to prevent longitudinal shrinkage therebetween as well as allowing the victim to be immobilized in various positions, for example in a sitting position. Thus, this splint essentially is secured to the upper and lower parts of the victim's body while leaving the pelvic area relatively unsecured to allow for positioning the victim in the desired position.

Further, the casing of this splint extends only up the sides of the victim and a single strap is then alternated between attachment points along the uppermost edges of the casing alongside the victim for adjusting the fit of the splint to the victim's body. Thus, the strap functions generally to hold the casing of the splint up alongside the victim until the splint is evacuated to produce a rigid form molded to the victim's body. In other words, the strap secures the victim to the splint, in the same manner as the straps on a backboard. Still further, the splint must be used as a whole for immobilizing the entire body of the victim, possibly limiting access to parts of the torso which may need to be examined and making it overly cumbersome and difficult to use in case of an emergency where only a certain body part of the victim needs to be immobilized. In addition, since this splint is intended for use with the victim's entire body, it is bulky and requires more space to store than a smaller splint intended for a specific body part. Also, and most importantly, the vacuum source necessary to rigidify the vacuum splint may not be readily available in an emergency situation.

Thus, there exists a need for a splint which is adapted for use in immobilizing the pelvis of a person in the event of an injury thereto. The splint should immobilize and prevent lateral displacement of the pelvis. Preferably, the splint should also be adapted to provide more than lateral immobilization for the pelvis, which further requires annular stabilization because of its ring-like structure. Further, the splint should be adjustable to fit the pelvic areas of various sizes of persons while being easily applied thereto. The splint should also not limit access to the victim's torso, since such access may be necessary for examination or for performing emergency procedures. In addition, the splint should be compact and readily and unobtrusively stored in an emergency response vehicle.

SUMMARY OF THE INVENTION

The above and other needs are met by the present invention which, in one advantageous embodiment, provides a pelvic splint comprising a flexible casing with a resiliently pliable padding layer disposed therein, a plurality of flexible members operably connected to the casing, and at least two straps operably connected to the casing for securing the casing about a pelvis. Preferably, the casing is adapted to substantially encircle and to stabilize the pelvis by immobilizing the pelvic ring and maintaining the annular integrity thereof in the event of a pelvic ring fracture injury. The casing is further preferably adapted to extend from about 5 centimeters to 10 centimeters above the iliac crest to about the middle third of the thighs.

In one embodiment, the casing is substantially rectangular and is oriented such that the larger dimension substantially encircles the pelvis. The flexible members are individually inserted into pockets disposed along the casing such that the flexible members extend parallel to the axis of the pelvic ring. The flexible members are then secured within the pockets by, for example, stitching or heat sealing the pockets. In one advantageous embodiment, three adjustable straps are operably connected to the casing in an orientation generally perpendicular to the flexible members and adapted to extend around the pelvis to secure the casing thereto.

Another advantageous aspect of the present invention comprises a method of stabilizing a pelvis in order to immobilize the pelvic ring and maintain the annular integrity thereof in the event of a pelvic ring fracture injury. First, a flexible casing is provided which has a padding layer disposed therein and a plurality of flexible members operably connected thereto. Preferably, the casing is adapted to extend about the pelvis such that the flexible members extend parallel to the axis of the pelvic ring. The casing is then wrapped about the pelvis such that the casing substantially encircles the pelvis and extends from above the iliac crest to about mid-thigh. The casing is then secured about the pelvis with at least two adjustable straps which are operably connected to the casing in a generally perpendicular orientation with respect to the flexible members, wherein the straps are also adapted to extend around the pelvis.

In an emergency situation, a tightly applied splint according to embodiments of the present invention will aid in annularly constraining the pelvis. As such, there will be a less severe effect on the victim since the annular integrity of the pelvis is preserved. The pelvic splint is also targeted for use in the prehospital environment and the emergency department where such features as compactness, ease of use, and unrestricted access to the victim's torso are important considerations. The pelvic splint of the present invention is small and easily applied to the victim by slipping the splint thereunder with minimal movement of the victim. The pelvic splint allows unrestricted access to the torso and lower extremities of the victim and allows procedures, such as radiography, to be performed while the splint is secured in place. The pelvic splint further permits the victim to be physically transferred without loss of immobilization of the pelvis. In addition, since the pelvic splint is specifically targeted at pelvic injuries, it is much smaller, less bulky, and less expensive than a full body immobilization splint.

Thus, a pelvic splint according to the present invention provides a splint for stabilizing the pelvis by immobilizing the same in order to maintain the annular integrity thereof in the event of a serious pelvic ring fracture injury, while also assisting in preventing lateral displacement of the injured pelvis. The pelvic splint can stabilize the pelvic area as applied and secured by the adjustable straps. Further, since it is intended for pelvic ring fracture injuries, the pelvic splint is small and not obtrusively bulky, it is easily applied to the victim, and it allows unrestricted access to the victim's torso.

BRIEF DESCRIPTION OF THE DRAWINGS

Some of the advantages of the present invention having been stated, others will appear as the description proceeds, when considered in conjunction with the accompanying drawings, which are not necessarily drawn to scale, in which:

FIG. 1A is a side elevation of a pelvic splint which embodies the features of the present invention.

FIG. 1B is a cross-sectional view of a pelvic splint according to the present invention taken along line 1B—1B in FIG. 1A.

FIG. 2 is a perspective view of a pelvic splint according to the present invention with a portion of the casing cut away to expose interior structure of the splint.

FIG. 3 is a plan view of the pelvic splint of the present invention, illustrating the splint as applied to the pelvis of a victim.

DETAILED DESCRIPTION OF THE INVENTION

Figure 4:
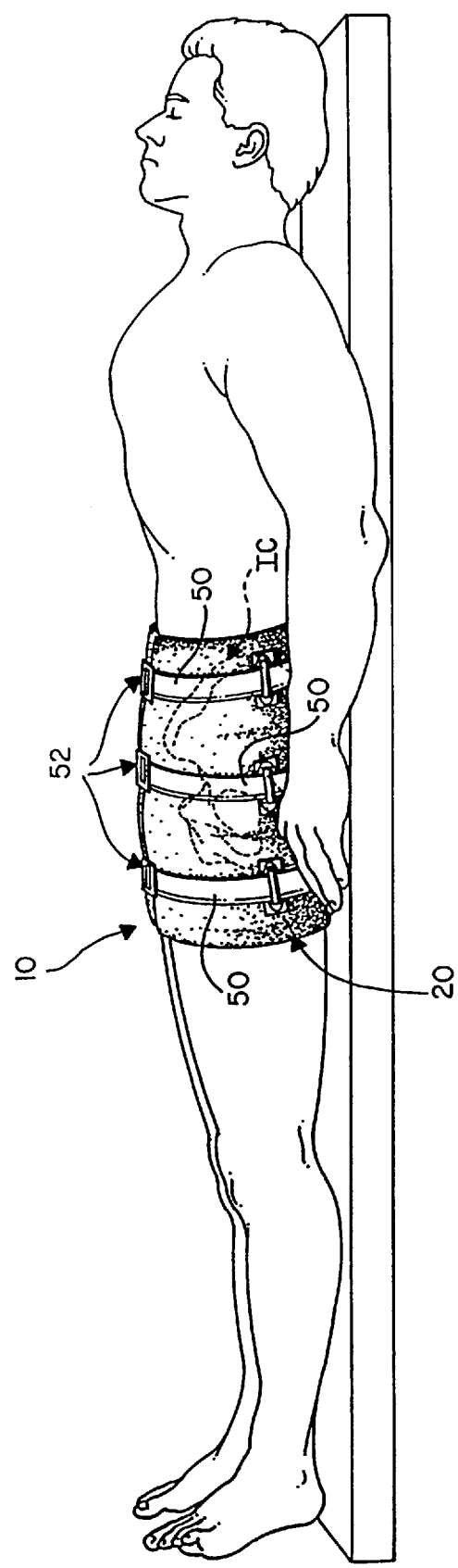
FIG. 4 is a side view of the pelvic splint of the present invention, illustrating the splint as applied to the pelvis of a victim.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Now referring to the drawings and, more particularly to FIGS. 1 and 2, there is disclosed an embodiment of a pelvic splint, indicated generally by the numeral 10, which includes the features of the present invention. The pelvic splint 10 generally comprises a flexible casing 20, a plurality of flexible members 30, a padding layer 40, and a plurality of adjustable straps 50. The splint 10 is used for immobilizing and maintaining the annular integrity of the pelvis in the event of a pelvic ring fracture. The splint 10 is readily implemented in an emergency situation in the field, but is also useful in the prehospital environment or the emergency department where such features as compactness, ease of use, and unrestricted access to the victim's torso are important considerations. More generally, the splint 10 may be used in situations where the pelvis must be immobilized to prevent serious injury to the victim.

As shown in FIG. 1, the casing 20 in one preferred embodiment comprises two generally rectangular sheets 22 of a durable and washable plastic, such as vinyl. The two sheets 22 are sealed together around the perimeters thereof to form the casing 20. The casing 20 may also be formed, for example, by folding over a single sheet of plastic and sealing the edges thereof or by sealing the ends of a tubular plastic extrusion. Forming the seal is accomplished by ultrasonic welding, by heat sealing, by adhesive, or the like. The result is a casing 20 forming an envelope having a durable seal. In addition, for the victim's comfort, the exterior surfaces of the casing 20 may have a fabric layer affixed thereto, wherein the fabric is also durable and washable. A generally rectangular casing 20 further comprises a pair of sides having a larger dimension 24 and a pair of sides having a smaller dimension 26. The larger dimension 24 is preferably adapted to substantially encircle the pelvis, while the smaller dimension 26 is preferably adapted to extend from above the iliac crest down to mid-thigh.

Embodiments of the splint 10 further include a plurality of flexible members 30 individually disposed within pockets 35 spaced apart about the casing 20. Preferably, the flexible members 30 are elongate and disposed within the casing 20 so as to extend parallel to the smaller dimension 26 of the casing 20 and approximately between the iliac crest and mid-thigh. The flexible members 30 may comprise, for instance, plastic strips or the like which are flexible and resilient, thereby providing reinforcement and stiffening of the casing 20. Stiffening of the casing 20 by the flexible members 30 may be useful, for example, in instances of an injury in addition to the pelvic fracture (such as a severe contusion) which may cause extreme discomfort to the patient if the splint 10 is tightly applied. In such instances, the flexible members 30 may help to distribute the compressive force imparted on the pelvis by the splint 10 over a larger area or may allow the splint 10 to be relatively loosely secured about the pelvis, thereby providing the necessary stabilization of the pelvis while alleviating some of the discomfort to the patient. The corresponding pockets 35 in which the flexible members 30 are disposed may be disposed within the casing 20 and between the sheets 22 or within one of the sheets 22. The flexible members 30 are secured in the pockets 35, for example, by stitching, heat sealing, adhesive, or the like such that the flexible members 30 are retained in a predetermined position about the casing 20. Preferably, the splint 10 further includes at least one padding layer 40 disposed within the casing 20 which serves as cushioning for the pelvis and increases the comfort level of the victim.

Embodiments of the splint 10 also include a plurality of straps 50 for securing the casing 20 about the pelvis of a victim. In one preferred embodiment, the splint 10 includes three adjustable straps 50, wherein the straps 50 extend along the larger dimension 24 of the casing 20 such that, when the splint 10 is wrapped around the pelvis of the victim, the straps 50 are capable of fully encircling the pelvis. Preferably, the straps 50 are operably coupled to the casing such that the straps 50 are oriented in a generally perpendicular relation with respect to the flexible members 30 about the casing 20. The straps 50 interact with the flexible members 30 within the casing 20 to form a web over which the compression forces imparted to the pelvis by the splint 10 may be distributed, thereby providing more even support to the fractured pelvis. The ends of the straps 50 preferably terminate in cooperating quick-connect connectors 52 which snap together and firmly secure the casing 20 about the pelvis. The quick-connect connectors 52 also provide for ready and rapid adjustment of the length of the straps 50 such that the splint 10 can be tightly and securely fastened around the pelvis. The quick-connect connectors of various types are well known to one skilled in the art and are not herein further described.

Now referring to FIGS. 3 and 4, a pelvic splint 10 is shown applied to the pelvis of a victim in lying in a prone position. The pelvic splint 10 according to embodiments of the present invention preferably extends from above the iliac crest down to about the middle of the victim's thighs. In one particularly advantageous embodiment, the splint 10 extends from between about 5 centimeters and about 10 centimeters above the iliac crest down to about the middle third of the thighs. The term iliac crest defines the uppermost point of the pelvic structure, of which there are actually two such iliac crests IC. The pelvis generally comprises two ilium bones and a pubic bone. The ilium generally engage at the posterior midpoint and arcuately extend around the sides of the pelvic area. The pubis connects both ilium on the anterior portion of the pelvis and completes a ring-like structure also called the pelvic ring. Each ilium houses a hip socket, into which a femur is connected, and extends upward from the hip socket in a fan-like structure. The uppermost part of each fan-like structure is an iliac crest IC which is located on either side of the body at approximately the waistline area.

The femur of each leg connects to the pelvis via the hip socket. Accordingly, subsequent to a pelvic ring fracture, movement of either femur before surgical fixation of the fracture will disrupt the annular integrity of the pelvis. Thus, it is important to restrict the movement of the femurs with respect to the pelvis in the event of a pelvic ring fracture to minimize the leverage produced when a femur is moved. As a result, effective immobilization of the pelvis requires that the pelvic splint cover the entire pelvis from at least the iliac crest IC on downward to about at least the middle third of the thighs to immobilize the femurs with respect to each other and with respect to the pelvis. Overlap of the splint at either extreme ensures full and optimum immobilization of the pelvis by minimizing lateral movement and preserving the annular integrity thereof.

To provide immobilization of the pelvis, the casing 20 extends up the sides of the victim and along the anterior portion of the pelvis. Once the casing 20 has been wrapped about the pelvis, the adjustable straps 50 encircle the casing 20 and connect, via the quick-connect connectors 52, about the anterior midline of the pelvis. The straps 50 are then adjusted such that the casing 20 is tightly secured around the pelvis of the victim and such that both a tangential and an axial compressive force are imparted on the pelvis. The force imparted by the secured splint 10 maintains the pelvic ring structure and stabilizes the pelvis in an emergency.

Figure 5:
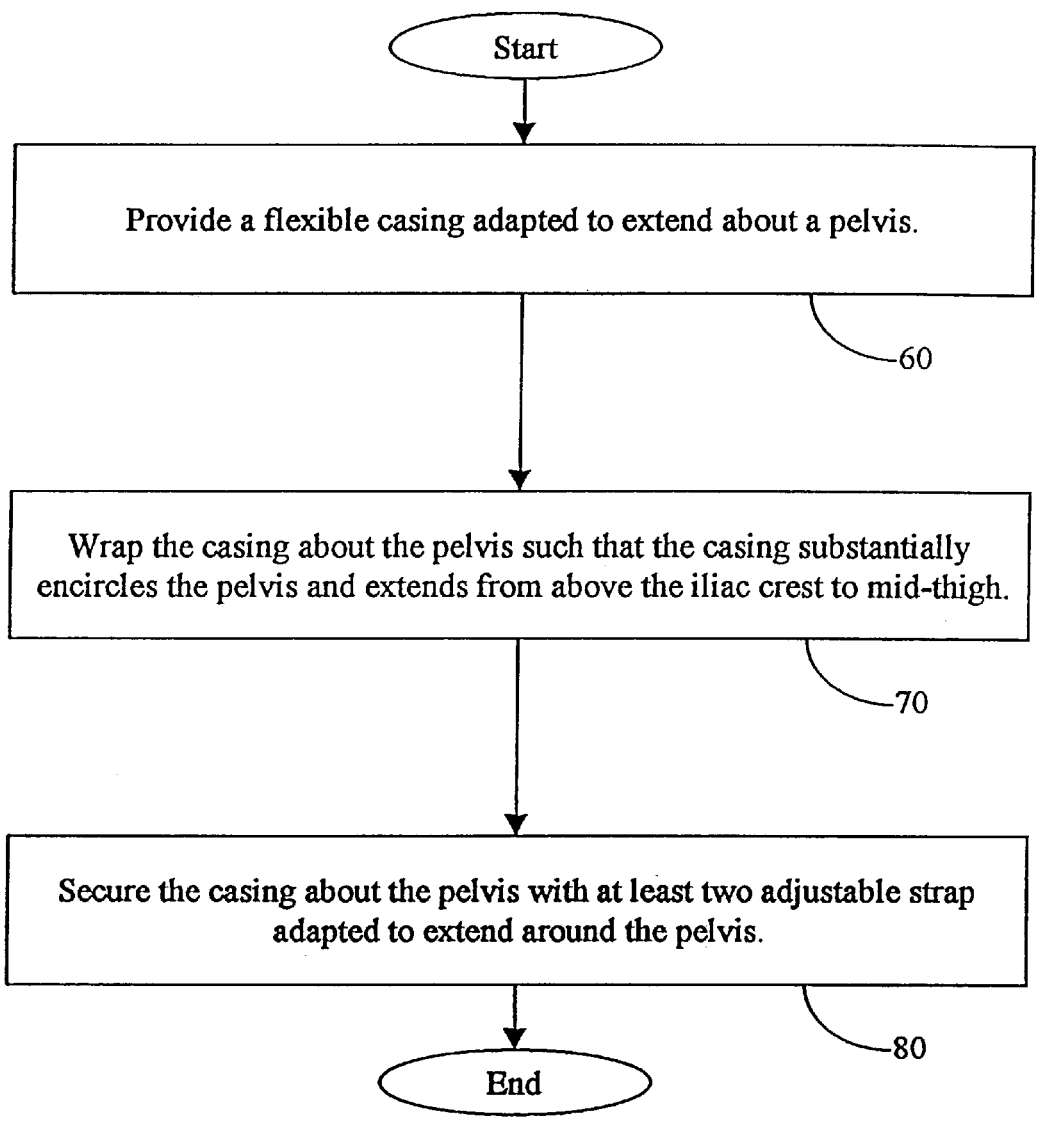
FIG. 5 is a flowchart illustrating a method of stabilizing a pelvis according to embodiments of the present invention.

Accordingly, a further advantageous aspect of the present invention is shown in FIG. 5 and comprises a method of stabilizing a pelvis in order to immobilize the pelvic ring and maintain the annular integrity thereof in the event of a pelvic ring fracture injury. First, a flexible casing is provided which is adapted to extend about the pelvis (block 60). Preferably, the casing includes a plurality of flexible members operably connected to the casing and adapted to extend parallel to the axis of the pelvic ring. In addition, embodiments of the present invention preferably include at least one pliable padding layer disposed within the casing for providing cushioning.

The casing is preferably substantially rectangular and is wrapped about the pelvis such that the casing substantially encircles the pelvis and extends from above the iliac crest to mid-thigh (block 70). In particularly advantageous embodiments, the casing extends from between about 5 centimeters and about 10 centimeters above the iliac crest down to about the middle third of the thighs. The casing is then secured about the pelvis with at least two adjustable straps operably connected to the casing, where the straps are adjusted such that the splint is snugly fastened about the pelvis (block 80). Preferably, three adjustable straps are provided which are connected to the casing in a generally perpendicular orientation with respect to the flexible members, where the straps are adapted to extend around the pelvis.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A pelvic splint comprising:

a substantially rectangular flexible casing having a larger dimension adapted to substantially encircle a pelvis, the casing being capable of stabilizing the pelvis by immobilizing the pelvic ring and maintaining the annular integrity thereof in the event of a pelvic ring fracture injury, the casing further having a smaller dimension adapted to extend only from above the iliac crest to mid-thigh;

at least one pliable padding layer disposed within the casing;

a plurality of flexible members operably connected to the casing and regularly and evenly spaced apart along the entire larger dimension of the casing, the flexible members further extending along the smaller dimension; and at least two adjustable straps operably connected to the casing and adapted to extend around the pelvis to secure the casing thereto, the straps cooperating with the casing to stabilize and maintain the annular configuration of the pelvic ring.

2. A pelvic splint according to claim 1 wherein the smaller dimension of the casing is adapted to extend from between about 5 centimeters and about 10 centimeters above the iliac crest to about the middle third of the thighs.

3. A pelvic splint according to claim 1 wherein the flexible members are individually inserted into pockets disposed along the larger dimension of the casing and the pockets then sealed using at least one of a stitching process and a heat sealing process to secure the flexible members therein.

4. A pelvic splint according to claim 1 wherein three adjustable straps are operably connected to the casing.

5. A pelvic according to claim 1 wherein the flexible members and the straps are operably connected to the casing such that the flexible members are oriented generally perpendicular to the straps.

* * * * *